US011185386B2

United States Patent
Liu et al.

(10) Patent No.: US 11,185,386 B2
(45) Date of Patent: Nov. 30, 2021

(54) SMART MARKING SYSTEM FOR SURGICAL VIDEO AND METHOD THEREOF

(71) Applicant: Taipei Medical University, Taipei (TW)

(72) Inventors: Wei Min Liu, Taipei (TW); Yu Chieh Lee, Taipei (TW); Yi Ta Shen, Taipei (TW)

(73) Assignee: Taipei Medical University, Taipei (TW)

( * ) Notice: Subject to any disclaimer, the term of this patent is extended or adjusted under 35 U.S.C. 154(b) by 164 days.

(21) Appl. No.: 16/547,707

(22) Filed: Aug. 22, 2019

(65) Prior Publication Data

US 2021/0052347 A1 Feb. 25, 2021

(51) Int. Cl.
*A61B 90/00* (2016.01)
*A61B 90/20* (2016.01)

(52) U.S. Cl.
CPC .............. *A61B 90/36* (2016.02); *A61B 90/20* (2016.02); *A61B 90/39* (2016.02); *A61B 2090/363* (2016.02); *A61B 2090/397* (2016.02); *A61B 2090/3983* (2016.02)

(58) Field of Classification Search
CPC ......... A61B 90/36; A61B 90/20; A61B 90/39; A61B 2090/3983; A61B 2090/363; A61B 2090/397; G11B 27/00; G11B 27/28; G11B 27/11
See application file for complete search history.

(56) References Cited

U.S. PATENT DOCUMENTS

| 2005/0113846 | A1* | 5/2005 | Carson | A61B 90/36 606/130 |
| 2016/0154844 | A1* | 6/2016 | Park | G06F 16/248 707/722 |
| 2018/0366231 | A1* | 12/2018 | Wolf | G16H 10/60 |
| 2019/0110856 | A1* | 4/2019 | Barral | A61B 90/37 |
| 2019/0138812 | A1* | 5/2019 | Sohn | G06K 9/6262 |
| 2019/0286652 | A1* | 9/2019 | Habbecke | G16H 20/40 |

* cited by examiner

*Primary Examiner* — Kim Y Vu
*Assistant Examiner* — Molly Delaney
(74) *Attorney, Agent, or Firm* — Chih Feng Yeh; Huntington IP Consulting Co., Ltd.

(57) ABSTRACT

A smart marking system for a surgical video and a method thereof are disclosed. The image recognition is performed for each surgical video to generate object information corresponding to each surgical video. The object information is used as feature data of the surgical video corresponding thereto. After a video to be analyzed is loaded, eigenvalue analysis and statistics are performed according to the video to be analyzed and all the feature data to calculate a similarity rate between the video to be analyzed and each surgical video. A surgical name corresponding to the surgical video with the highest similarity rate is selected to mark as a surgical name corresponding to the video to be analyzed. The video to be analyzed and the surgical name corresponding thereto are stored in a database as the surgical video. Thus, the efficiency of marking the surgical videos is improved.

6 Claims, 7 Drawing Sheets

SMART MARKING SYSTEM FOR SURGICAL VIDEO AND METHOD THEREOF

BACKGROUND

1. Technical Field

The present invention relates to a marking system and a method thereof. In particular, the invention pertains to a smart marking system for a surgical video and a method thereof.

2. Description of Related Arts

In recent years, with the popularization and vigorous development of medical technology, various related applications have sprung up, and the value-added application of the surgery videos has attracted the most attention.

In general, surgery videos can be used to provide learning for doctors, students, or related practitioners, and can even be used as surgical records to avoid medical disputes. However, because the type of surgery is very complicated, it is necessary to mark the surgical videos for easy browsing; for instance, recording the surgical procedure, the organ and the surgeon. As a result, all relevant surgical videos can be quickly queried based on the marked information. Nevertheless, in the past, the method of manually determining and marking surgical videos is prone to problems such as an increase in error rate and inefficiency due to fatigue.

In the light of this, some manufacturers have proposed a technique combining with image recognition, which is used to automatically classify and mark organs appearing in a surgical video through organ identification technology, thereby improving the error rate of marking and improving the efficiency of marking. However, this method can be used for the general classification of organs, but the surgical procedure cannot be identified. Therefore, it is still necessary to rely on professional medical personnel to determine the surgical procedure and perform supplementary marking, so there is still a problem with poor efficiency in marking surgical videos.

In summary, it can be seen that there is a problem with poor efficiency in marking surgical videos in the prior art. Therefore, it is necessary to propose an improved technical solution to solve this problem.

SUMMARY

In view of the prior art, there is a problem with poor efficiency in marking surgical videos, and the present invention discloses a smart marking system for a surgical video and a method thereof.

The smart marking system for the surgical video disclosed in the present invention comprises a database, a feature generation module, an analysis module and a storage module. The database is used to store a plurality of the surgical videos, and each of the plurality of the surgical videos corresponds to a surgical name. The feature generation module is connected to the database for loading each of the plurality of the surgical videos of the database for image recognition separately at the beginning, and generating at least one object information corresponding to each of the plurality of the surgical videos according to each image recognition result, and using the at least one object information as feature data of the surgical video corresponding thereto, and storing the feature data in the database, wherein each of the at least one object information comprises coordinates, proportions and time points of an image object existing in the surgical video corresponding thereto. The analysis module is connected to the database for performing eigenvalue analysis and statistics according to a video to be analyzed and all the feature data after loading the video to be analyzed to calculate a similarity rate between the video to be analyzed and each of the plurality of the surgical videos. The storage module is connected to the analysis module for selecting the surgical name corresponding to the surgical video with the highest similarity rate to mark a surgical name corresponding to the video to be analyzed, and storing the video to be analyzed and the surgical name corresponding thereto in the database to make the video to be analyzed as one of the surgical videos of the database.

The smart marking method for the surgical video disclosed in the present invention comprises the steps of: providing a plurality of surgical videos in a database, each of the plurality of the surgical videos corresponding to a surgical name; loading each of the plurality of the surgical videos of the database separately for image recognition at the beginning, and generating at least one object information corresponding to each of the plurality of the surgical videos according to each image recognition result, and using the at least one object information as feature data of the surgical video corresponding thereto, and storing the feature data in the database, wherein each of the at least one object information comprises coordinates, proportions and time points of an image object existing in the surgical video corresponding thereto; performing eigenvalue analysis and statistics according to a video to be analyzed and all the feature data after loading the video to be analyzed to calculate a similarity rate between the video to be analyzed and each of the plurality of the surgical videos; and selecting the surgical name corresponding to the surgical video with the highest similarity rate to mark a surgical name corresponding to the video to be analyzed, and storing the video to be analyzed and the surgical name corresponding thereto in the database to make the video to be analyzed as one of the surgical videos of the database.

The system and method disclosed by the present invention are as above, and the difference from the prior art is that performing image recognition for each surgical video to generate the object information corresponding thereto, using the generated object information as feature data of the surgical video corresponding thereto, performing eigenvalue analysis and statistics according to the video to be analyzed and all the feature data after loading the video to be analyzed to calculate the similarity rate of the video to be analyzed and each surgical video; selecting the surgical name corresponding to the surgical video with the highest similarity rate to mark as the surgical name corresponding to the video to be analyzed; and storing the video to be analyzed and the surgical name corresponding thereto in the database to make the video to be analyzed as one of the surgical videos of the database.

Above-mentioned technical means can be used to solve the problems of the prior art, and to achieve the technical effect of improving the efficiency of marking surgical videos.

BRIEF DESCRIPTION OF THE DRAWINGS

The structure, operating principle and effects of the present invention will be described in detail by way of various embodiments which are illustrated in the accompanying drawings.

DETAILED DESCRIPTION

Figure 1:
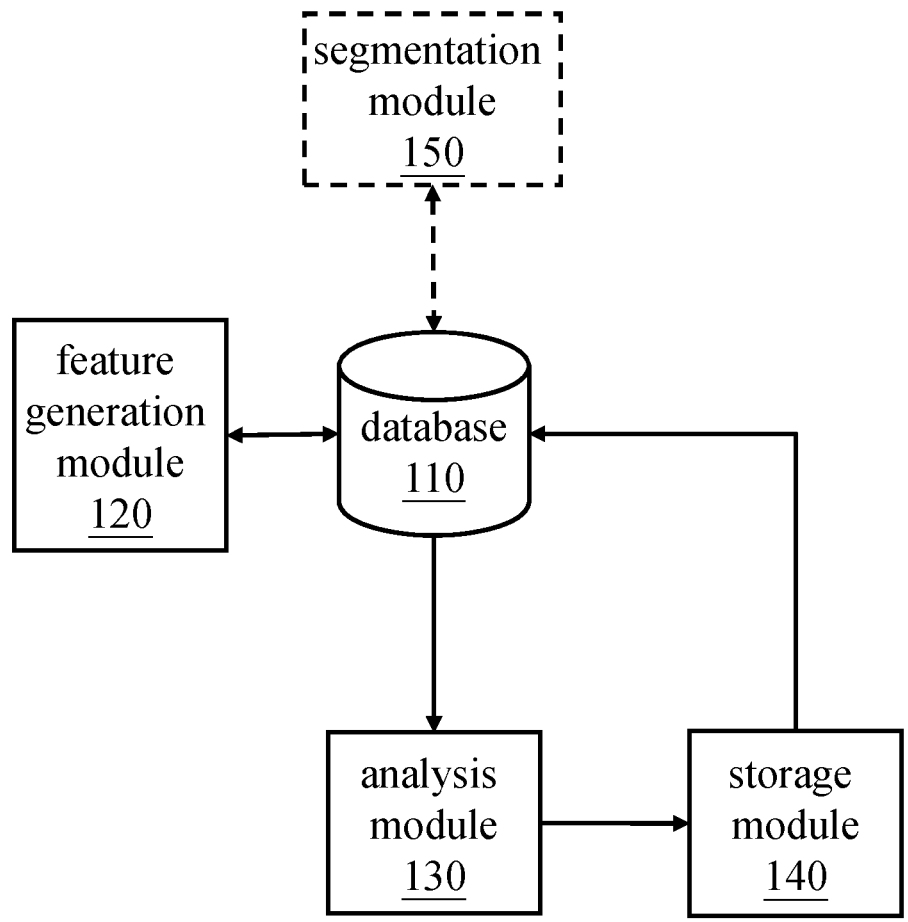
FIG. 1 is a system architecture diagram of a smart marking system for a surgical video according to the present invention.

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also comprised within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

As used herein, the term "or" comprises any and all combinations of one or more of the associated listed items. It will be understood that when an element is referred to as being "on" "connected to" or "coupled to" another element, it can be directly on, connected or coupled to the other element, or intervening elements may be present. In contrast, when an element is referred to as being "directly on" "directly connected to" or "directly coupled to" another element, there are no intervening elements present.

In addition, unless explicitly described to the contrary, the word "comprise" and variations, such as "comprises" or "comprising", will be understood to imply the inclusion of stated elements but not the exclusion of any other elements.

Before describing a smart marking system for a surgical video and a method thereof disclosed in the present invention, the nouns defined by the present invention are explained first. The "surgical name" in the present invention refers to the name of the surgical procedure, such as "hysterectomy" and "myomectomy". The "object information" is information generated by image recognition technology such as an organ and a surgical instrument. For example, the organ in the surgical video is identified by the organ recognition technology, an image of the organ is taken as an image object, and the image object and its coordinates, proportions and time points in the surgical video are used as the object information. In other words, an article that can be recognized by image recognition technology is called an object, and the object information records the detailed information of the object, such as the coordinates, proportions and time points at which the object appears.

The smart marking system for the surgical video and the method thereof according to the present invention are further described below with reference to the drawings. Please refer to FIG. 1, FIG. 1 is a system architecture diagram of a smart marking system for a surgical video according to the present invention. The smart marking system comprises a database 110, a feature generation module 120, an analysis module 130, and a storage module 140. The database 110 is used to store surgical videos, and each surgical video corresponds to a surgical name. In practical implementation, the database 110 can be implemented using a relational database, a NoSQL database, and the like. In addition, the database 110 can store the organ eigenvalues and the surgical instrument eigenvalues for loading when the feature generation module 120 performing image recognition on surgical videos. The feature generation module 120 extracts an image that matches one of the organ eigenvalues or the surgical instrument eigenvalues in the surgical video as an image object of the object information, and coordinates, proportions and time points in which the image object exists in the surgical video are recorded in the object information. The organ eigenvalues or the surgical instrument eigenvalues can be generated through a neural network (NN), deep learning, etc. For example, a large number of images of organs and surgical instruments are used as training materials in advance to generate corresponding eigenvalues, namely: the organ eigenvalues and the surgical instrument eigenvalues.

The feature generation module 120 is connected to the database 110. The feature generation module 120 is used to load the surgical videos of the database 110 for image recognition separately, generate object information corresponding to each surgical video according to each image recognition result, use the object information as feature data of the surgical video corresponding thereto, and store the feature data in the database 110. Each object information comprises coordinates, proportions and time points in which the image object exists in the corresponding surgical video. In practice, the generated object information can only retain the parts related to the key organs, while the object information of other non-critical organs is deleted. The key organs are determined according to the coordinates and proportion of the image objects. For example, when the image object of the organ is located at the center of the surgical video or the proportion which the image object of the organ occupies in the surgical video is larger than the preset value, the organ is the key organ. In addition, the feature generation module 120 can also load all the surgical videos corresponding to the same surgical name to identify the type of the surgical instrument and the type, shape and size of the abnormal organ, and generate the starting eigenvalue corresponding to the surgical name according to each identification result, and store each starting eigenvalue and its corresponding surgical name in the database 110. In practical implementation, the method of generating the starting eigenvalues and the above-described method of generating the organ eigenvalues and the surgical instrument eigenvalues are the same.

The analysis module 130 is connected to the database 110. The analysis module 130 is used to perform eigenvalue analysis and statistics according to the video to be analyzed and all the feature data after loading the video to be analyzed, so as to calculate the similarity rate between the video to be analyzed and each surgical video. The video to be analyzed refers to a surgical video that has not been marked with a surgical name. In actual implementation, since the feature generation module 120 has generated corresponding feature data according to each of the surgical videos, the analysis module 130 performs eigenvalue analysis and statistics on the video to be analyzed and each feature data, and then calculates the similarity rate between the video to be analyzed and each surgical video. For example, the similarity rate between the video to be analyzed and the first surgical video is 90%, and the similarity rate between the video to be analyzed and the second surgical video is 40%. In addition, when the database 110 stores the starting eigenvalues, the analysis module 130 can also compare the loaded video to be analyzed with the starting eigenvalues in the database 110, and load the surgical name corresponding to the starting eigenvalue that matches the video to be analyzed. When the loaded surgical name is different from the surgical name selected according to the similarity rates, a prompt message is generated and the loaded surgical name or the surgical name selected according to the similarity rates is chosen to be the surgical name corresponding to the video to be analyzed. For example, it is assumed that the loaded surgical name is "total hysterectomy", and the surgical name selected according to the similarity rates is "subtotal hysterectomy", at which point a prompt message is generated for display and the user is allowed to choose one of them as the surgical name corresponding to the video to be analyzed, and even the user can type the text to specify the surgical name. In particular, in actual implementation, the analysis module 130 can adjust the similarity rate according to whether the key organ (for example, the organ with the largest proportion of the video, or the organ at a central position) has the solid tissue or the abnormality of the tumor margin cells. Taking the above-mentioned video to be analyzed, the first surgical video as an example, it is assumed that the key organ of the video to be analyzed does not have a solid tissue, and the key organ of the first surgical video has a solid tissue, then the similarity rate between the video to be analyzed and the first surgical video can be reduced. For instance, the similarity rate is reduced from 90% to 80%. Conversely, if both the video to be analyzed and the first surgical video have the solid tissue and the abnormality of the tumor margin cells in the video to be analyzed is similar to that in the first surgical video, the similarity rate can increase. Although the present invention exemplifies the adjustment method of the similarity rate as described above, the present invention is not limited thereto, and any method for further adjusting the similarity rate according to the difference of organs, tissues, cells or surgical instruments appearing in the video does not depart from the scope of application of the present invention. For example, the type of surgical instrument, environmental determination (such as ovary), abnormal organs (such as cysts), medical statistical information (for example, about 80% to 85% of ovarian tumors are benign), the instantaneous screen ratio of liquid outflow, liquid color, and the like are parameters of the analysis.

The storage module 140 is connected to the analysis module 130, and is configured to select a surgical name corresponding to the surgical video with the highest similarity rate to mark the surgical name corresponding to the video to be analyzed, and store the video to be analyzed and the surgical name corresponding thereto in the database 110 to make the video to be analyzed as one of the surgical videos. For example, if there is the highest similarity rate between the video to be analyzed and the third surgical video, and the surgical name corresponding to the third surgical video is "myomectomy", then the storage module 140 marks the surgical name corresponding to the third surgical video as "myomectomy" as the surgical name corresponding to the video to be analyzed, and stores the video to be analyzed and its corresponding surgical name "myomectomy" in the database 110 to make the video to be analyzed as one of the surgical videos. In this way, after inputting the video to be analyzed, the video to be analyzed can be quickly marked with the corresponding surgical name, and can even be classified and stored according to the marked surgical name. For example, the same surgical name is the same class, and the surgical videos corresponding to the same surgical name are stored in the same folder.

In addition, the system of the present invention may further comprise a segmentation module 150 for detecting a plurality of time points in each surgical video in which at least one of the organ eigenvalues and the surgical instrument eigenvalues is present when the organ eigenvalues and the surgical instrument eigenvalues are stored in the database 110. When a time interval between the adjacent time points in which at least one of the organ eigenvalues and the surgical instrument eigenvalues is present is greater than a predetermined interval, the segmentation module 150 deletes a plurality of frames corresponding to the time interval in each surgical videos to form a plurality of divided videos, and stores the plurality of divided videos in the database 110. In other words, the videos with organs and surgical instruments or either is retained, and the videos without organs or surgical instruments are deleted. In practice, it is common to retain videos with organs and surgical instruments as key videos. By the above method, unimportant videos can be deleted, and even multiple divided videos can be reconstructed into a single video to achieve the effect of editing the essence fragments.

It should be noted that, in actual implementation, each module described in the present invention may be implemented in various manners, including software, hardware, or any combination thereof. For example, in some embodiments, each module can be implemented by using software and hardware or one of them. In addition, the present invention can also be implemented partially or completely based on hardware. For example, one or more modules in the system can be implemented by integrated circuit chips, system on chips (SoC), complex programmable logic devices (CPLD), and field programmable gate arrays (FPGA). The present invention can be a system, a method and/or a computer program. The computer program can comprise a computer readable storage medium having computer readable program instructions for causing a processor to implement various aspects of the present invention. The computer readable storage medium can be tangible for retaining and storing instructions used by the instruction execution device. The computer readable storage medium can be, but is not limited to, an electrical storage device, a magnetic storage device, an optical storage device, an electromagnetic storage device, a semiconductor storage device, or any suitable combination of the foregoing. More specific examples (non-exhaustive lists) of the computer readable storage medium comprise: a hard disk, a random access memory, a read only memory, a flash memory, an optical disk, a floppy disk, and any suitable combination of the foregoing. The computer readable storage medium as used herein is not to be interpreted as a transient signal itself, such as a radio wave or other freely propagating electromagnetic wave, an electromagnetic wave propagating through a waveguide or other transmission medium (e.g., an optical signal through a fiber optic cable), or an electrical signal transmitted through a wire. In addition, the computer readable program instructions described herein can be downloaded from the computer readable storage medium to various computing/processing devices or downloaded to an external computer device or an external storage device through a network such as the Internet, a local area network, a wide area network, and/or a wireless network. The network may comprise copper transmission cables, fiber optic transmissions, wireless transmissions, routers, firewalls, switches, hubs, and/or gateways. A network card or network interface in each computing/processing device receives computer readable program instructions from the network and forwards the computer readable program instructions for storage in the computer readable storage medium in each computing/processing device. The computer program instructions for performing the operations of the present invention may be combined language instructions, instruction set architecture instructions, machine instructions, machine related instructions, microinstructions, firmware instructions, or source code or object code written in any combination of one or more programming language, wherein the programming language comprises object-oriented programming languages such as Common Lisp, Python, C++, Objective-C, Smalltalk, Delphi, Java, Swift, C#, Perl, Ruby, and PHP, and conventional procedural programming languages, such as C language or similar programming language. The computer readable program instructions can be executed entirely on the computer, partly on the computer, as a standalone software, partly on the client computer, partly on the remote computer, or entirely on the remote computer or server.

Figure 2A:
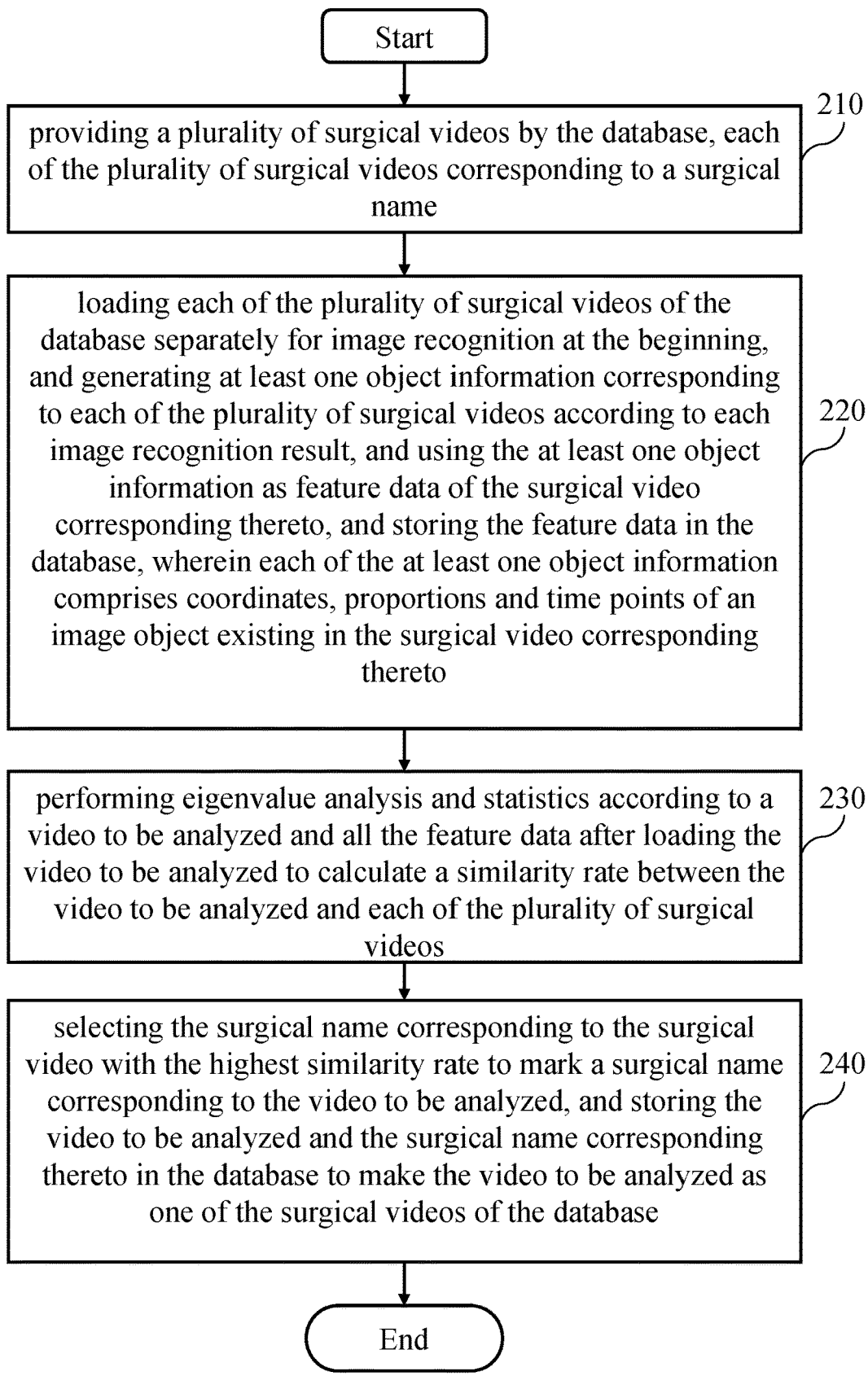
FIG. 2A to FIG. 2C is a flow chart of a smart marking method for the surgical video according to the present invention.
Figure 2B:
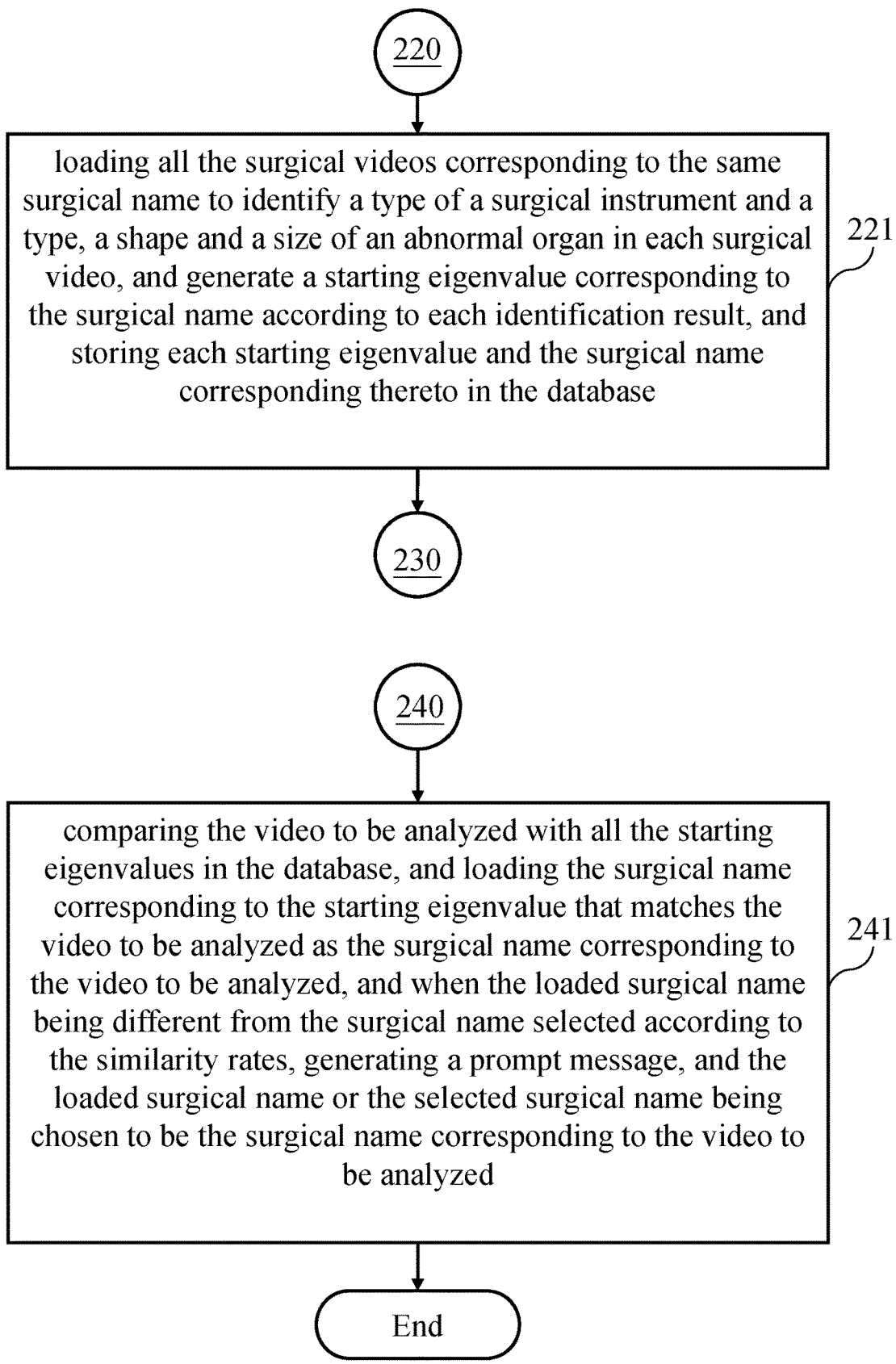
Figure 2C:
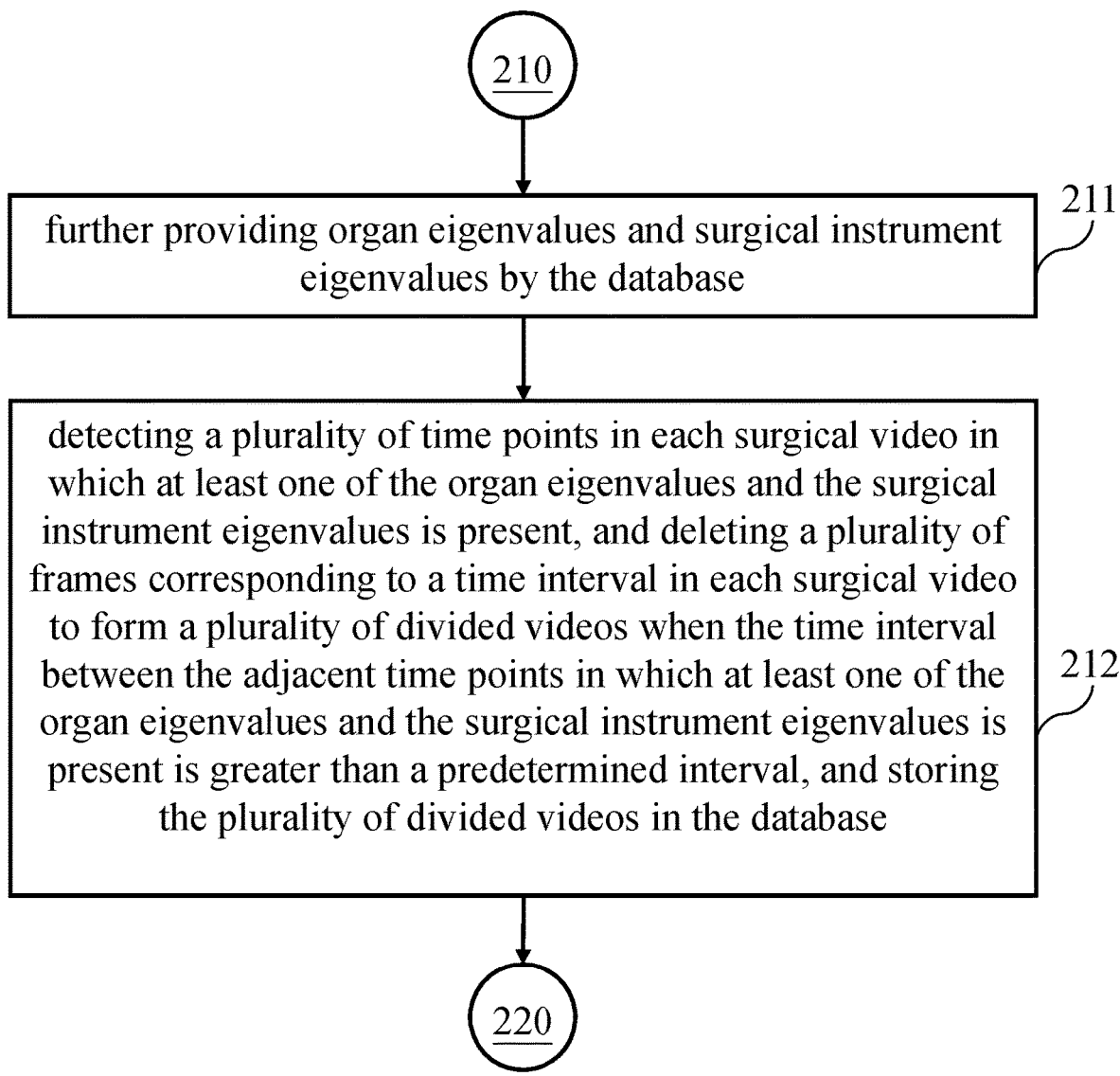

Please refer to FIG. 2A to FIG. 2C, and FIG. 2A to FIG. 2C is a flow chart of a smart marking method for the surgical video according to the present invention. The steps of the smart marking method comprise: providing a plurality of surgical videos by the database 110, each of the plurality of surgical videos corresponding to a surgical name (step 210); loading each of the plurality of surgical videos of the database 110 separately for image recognition at the beginning, and generating at least one object information corresponding to each of the plurality of surgical videos according to each image recognition result, and using the at least one object information as feature data of the surgical video corresponding thereto, and storing the feature data in the database 110, wherein each of the at least one object information comprises coordinates, proportions and time points of an image object existing in the surgical video corresponding thereto (step 220); performing eigenvalue analysis and statistics according to a video to be analyzed and all the feature data after loading the video to be analyzed to calculate a similarity rate between the video to be analyzed and each of the plurality of surgical videos (step 230); and selecting the surgical name corresponding to the surgical video with the highest similarity rate to mark a surgical name corresponding to the video to be analyzed, and storing the video to be analyzed and the surgical name corresponding thereto in the database 110 to make the video to be analyzed as one of the surgical videos of the database 110 (step 240). Through the above steps, the image recognition is performed for each surgical video to generate object information corresponding to each surgical video, the object information is used as feature data of the surgical video corresponding thereto, eigenvalue analysis and statistics are performed according to the video to be analyzed and all the feature data to calculate the similarity rate between the video to be analyzed and each surgical video after the video to be analyzed is loaded, the surgical name corresponding to the surgical video with the highest similarity rate is selected to mark as the surgical name corresponding to the video to be analyzed, and the video to be analyzed and the surgical name corresponding thereto are stored in the database 110 as the surgical video.

In addition, as shown in FIG. 2B, after step 220, the method further comprises the step of loading all the surgical videos corresponding to the same surgical name to identify a type of a surgical instrument and a type, a shape and a size of an abnormal organ in each surgical video, and generate a starting eigenvalue corresponding to the surgical name according to each identification result, and storing each starting eigenvalue and the surgical name corresponding thereto in the database 110 (step 221); and after step 240, the method further comprises the step of comparing the video to be analyzed with all the starting eigenvalues in the database, and loading the surgical name corresponding to the starting eigenvalue that matches the video to be analyzed as the surgical name corresponding to the video to be analyzed, and when the loaded surgical name being different from the surgical name selected according to the similarity rates, generating a prompt message, and the loaded surgical name or the selected surgical name being chosen to be the surgical name corresponding to the video to be analyzed (step 241). In addition, as shown in FIG. 2C, after step 210, the method further comprises the steps of further providing organ eigenvalues and surgical instrument eigenvalues by the database 110 (step 211); and detecting a plurality of time points in each surgical video in which at least one of the organ eigenvalues and the surgical instrument eigenvalues is present, and deleting a plurality of frames corresponding to a time interval in each surgical video to form a plurality of divided videos when the time interval between the adjacent time points in which at least one of the organ eigenvalues and the surgical instrument eigenvalues is present is greater than a predetermined interval, and storing the plurality of divided videos in the database 110 (step 212).

Figure 3:
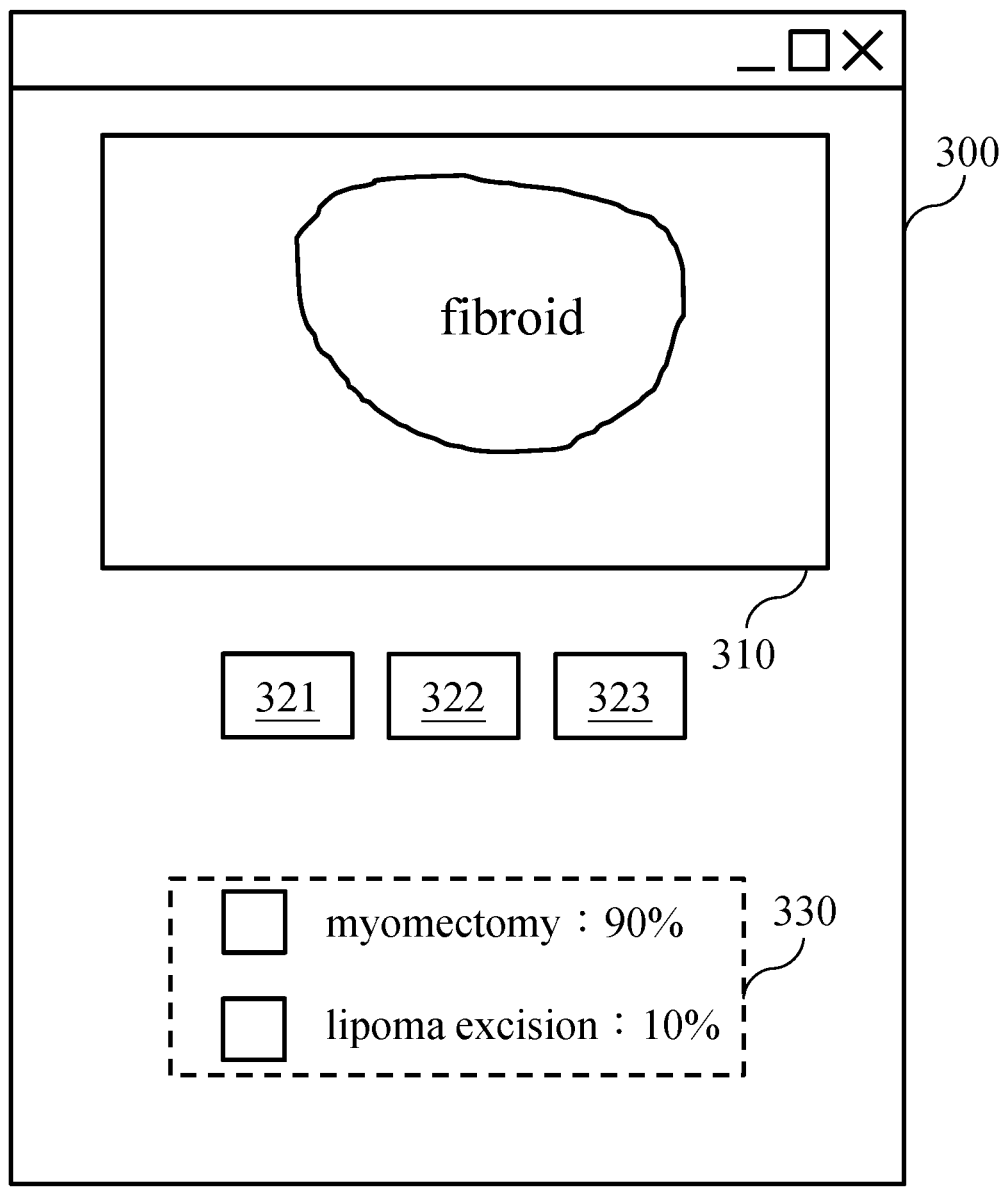
FIG. 3 is a schematic diagram of determining a surgical name of a video to be analyzed and marking it by applying the present invention.

The following description will be made by way of example with reference to FIG. 3 to FIG. 5. Please refer to FIG. 3, and FIG. 3 is a schematic diagram of determining a surgical name of a video to be analyzed and marking it by applying the present invention. It is assumed that, at the beginning, the feature data has been generated for each surgical video of the database 110. After the user opens the display window 300 and selects the loading component 321 by the cursor, the video to be marked can be selected as the loaded video to be analyzed, and the video to be analyzed is displayed in the playing block 310. Then, the user can click the analyzing component 322 to perform eigenvalue analysis and statistics on the video to be analyzed and all the feature data in the database 110 to calculate the similarity rate between the video to be analyzed and each surgical video. It is assumed that two surgical videos have been stored in the database 110, wherein the first surgical video corresponds to the surgical name "myomectomy", and the second surgical video corresponds to the surgical name "lipoma excision". After the similarity rates are calculated, the similarity rate between the video to be analyzed and the first surgical video is 90%, and the similarity rate between the video to be analyzed and the second surgical video is 10%. At this time, as shown in FIG. 3, according to the similarity rates, the surgical name corresponding to the surgical video and its corresponding similarity rate are sequentially displayed in the surgical name block 330, and the surgery name "myomectomy" corresponding to the surgical video with the highest similarity rate is directly marked as the surgical name corresponding to the video to be analyzed. In particular, if the similarity rates are very close, the user can also select the playback component 323 to play the video to be analyzed, and then directly select the appropriate surgical name in the surgical name block 330 according to the browsing result of the video to be analyzed to mark the surgical name corresponding to the video to be analyzed. After the marking is completed, the video to be analyzed and its corresponding surgical name can be stored in the database 110 to make the video to be analyzed as a surgical video. In addition, in order to improve the efficiency of the marking, the above process can also be processed by the batch operation mode. For example, multiple videos to be analyzed are simultaneously loaded and marked one by one, and the marking method is to directly mark the surgical name corresponding to the surgical video with the highest similarity rate as the surgical name corresponding to the current video to be analyzed, without the need to provide the user to select the surgical name and browse the video to be analyzed, thereby greatly improving the marking efficiency.

Figure 4:
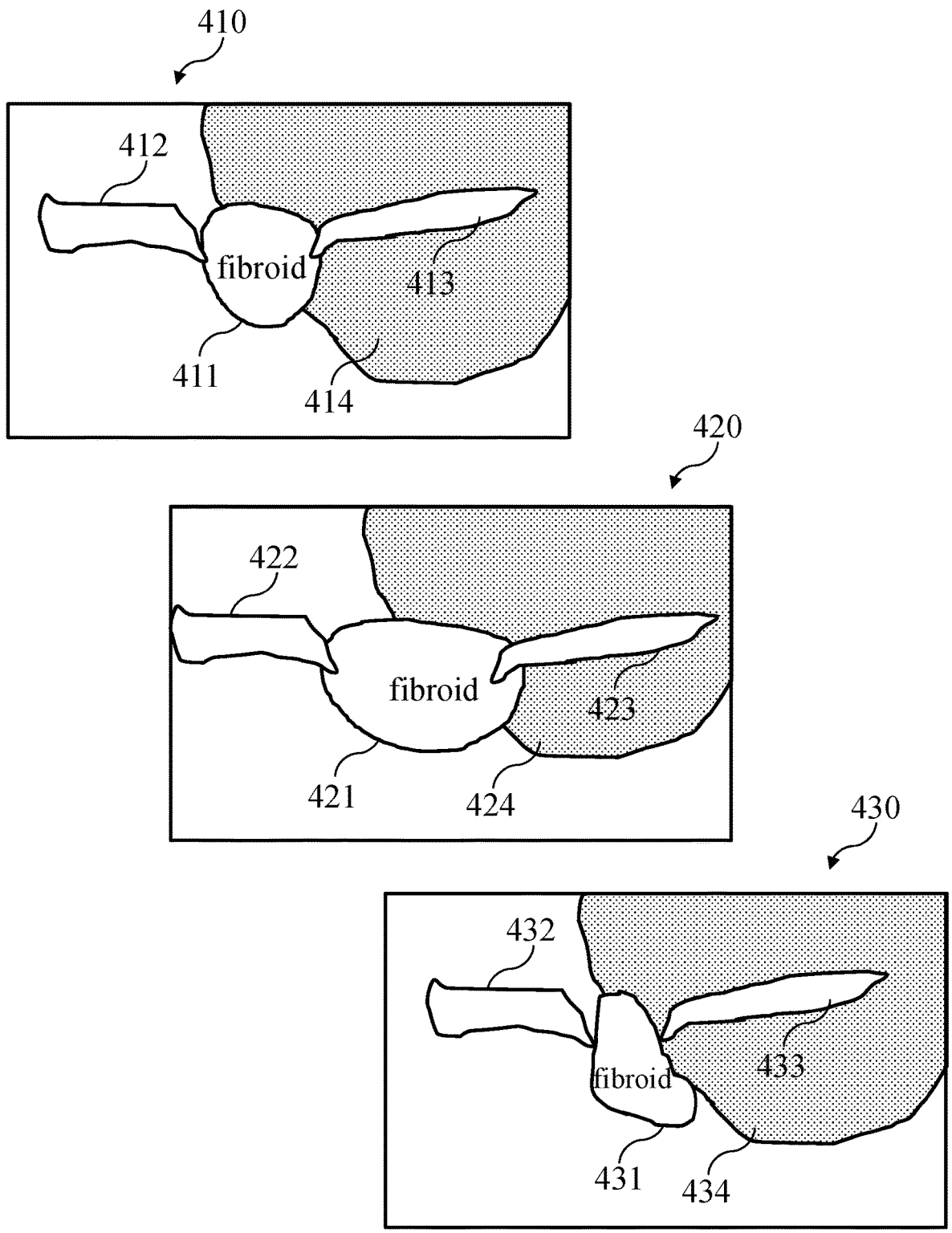
FIG. 4 is a schematic diagram of generating a starting eigenvalue by applying the present invention.

As shown in FIG. 4, FIG. 4 is a schematic diagram of generating a starting eigenvalue by applying the present invention. It is assumed that the database 110 has a plurality of surgical videos stored in advance, and each surgical video corresponds to a surgical name. The user can first make all surgical videos corresponding to the same surgical name be loaded to identify the type of the surgical instrument and the type, shape and size of the abnormal organ in each surgical video, and generate a starting eigenvalue corresponding to the surgical name according to each identification result, and each starting eigenvalue and its corresponding surgical name are stored in the database 110. Take the surgical name "myomectomy" as an example. The user can first make the beginning of all the surgical videos (410, 420 and 430) corresponding to the surgical name be loaded, and these loaded parts are used as training samples to generate the starting eigenvalues corresponding thereto by a neural network or deep learning. During the training process, there are the same type of first surgical instrument, namely: the first surgical instrument (412, 422, 432), the same type of second surgical instrument, namely: the second surgical instrument (413, 423, 433) in all surgical videos, and all surgical videos also have the uterus (414, 424, and 434) and the fibroid (411, 421, and 431). Therefore, even if there are slight differences in position, size, and shape, each starting eigenvalue corresponding to the surgical name "myomectomy" can still be generated after the training through the neural network or deep learning is finished. That is to say, under the premise that the initial actions of the surgical videos corresponding to the same surgical name are similar, the starting eigenvalue corresponding to each surgical video can be established by the neural network or deep learning. By such analogy, each surgical name and its corresponding starting eigenvalues can be established.

Figure 5:
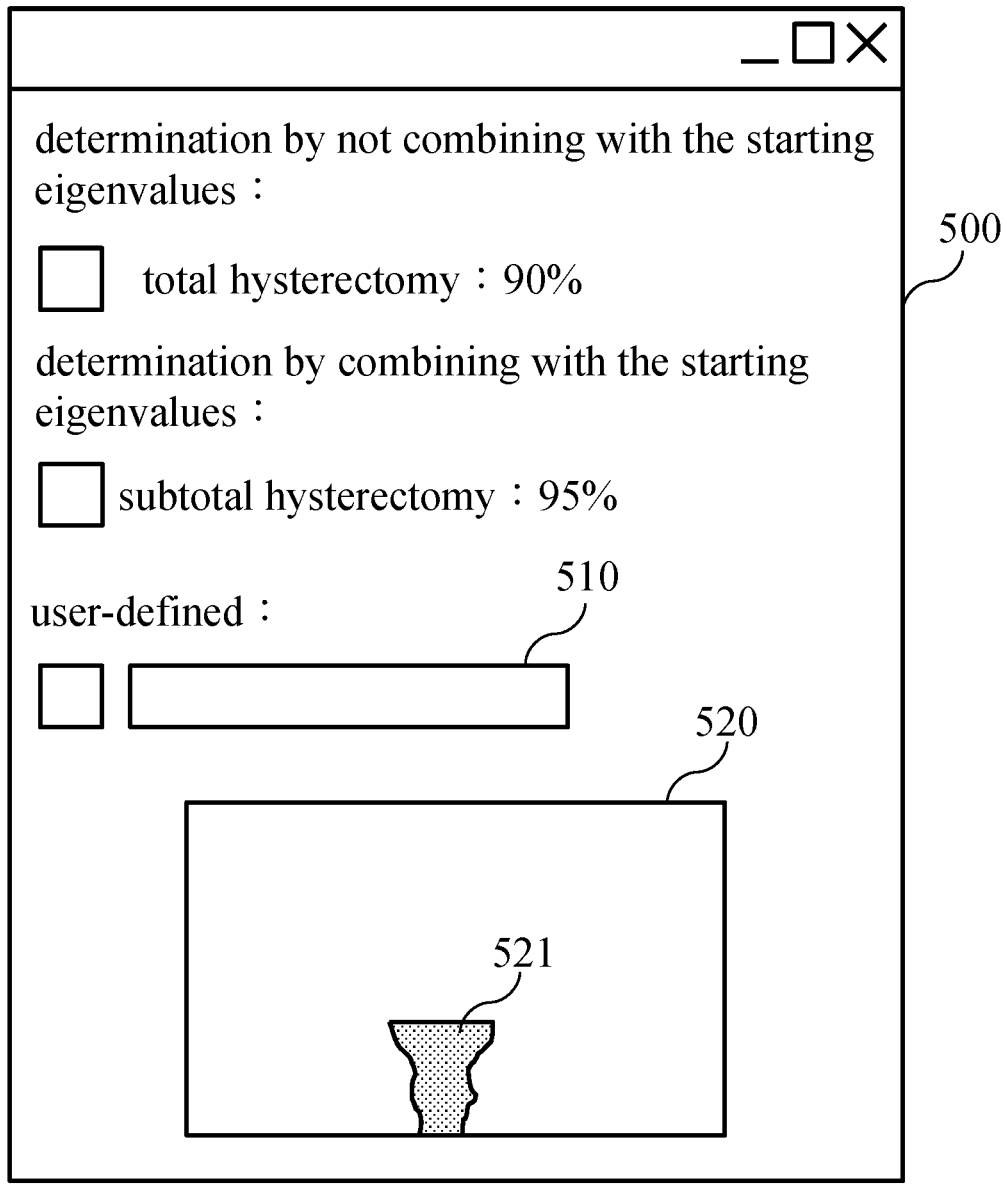
FIG. 5 is a schematic diagram of combining with the starting eigenvalues to determine the surgical name by applying the present invention.

Please refer to FIG. 5, and FIG. 5 is a schematic diagram of combining with the starting eigenvalues to determine the surgical name by applying the present invention. After each surgical name and its corresponding starting eigenvalues can be established, in addition to performing eigenvalue analysis and statistics on the video to be analyzed and all the feature data to calculate the similarity rate between the video to be analyzed and each surgical video, the analysis module 130 can compare the loaded video to be analyzed with all the starting eigenvalues, and the surgical name corresponding to the starting eigenvalue that matches the video to be analyzed (e.g., the highest similarity rate) is loaded. In other words, in addition to selecting the surgical name corresponding to the surgical video with the highest similarity rate (for example, "myomectomy"), the surgical name corresponding to the starting eigenvalue that matches the video to be analyzed (for example, "myomectomy") is also loaded. In general, the loaded surgical name is the same as the selected surgical name according to the similarity rates of the surgical videos, so the surgical name can be directly marked as the surgical name of the video to be analyzed. However, it is assumed that the loaded surgical name and the selected surgical name according to the similarity rates of the surgical videos are different (for example, the former surgical name is total hysterectomy; the latter surgical name is subtotal hysterectomy). At this time, the prompt message 500 can be generated as shown in FIG. 5, and the user is allowed to select one of the surgical names "total hysterectomy" and "subtotal hysterectomy" as the surgical name corresponding to the video to be analyzed. In order to help the user to select the appropriate surgical name, the video to be analyzed can also be played in the playback block 520 for the user to browse. In this case, since the presence of the cervix 521 can be seen in the video, it is appropriate to select the surgical name "subtotal hysterectomy". In addition, if there is no proper surgical name, the user can directly type the appropriate surgical name in the input block 510 to correspond to the video to be analyzed, thereby completing the marking.

In summary, it can be seen that the difference between the present invention and the prior art is that performing image recognition for each surgical video to generate the object information corresponding thereto, using the generated object information as feature data of the surgical video corresponding thereto, performing eigenvalue analysis and statistics according to the video to be analyzed and all the feature data after loading the video to be analyzed to calculate the similarity rate of the video to be analyzed and each surgical video; selecting the surgical name corresponding to the surgical video with the highest similarity rate to mark as the surgical name corresponding to the video to be analyzed; and storing the video to be analyzed and the surgical name corresponding thereto in the database to make the video to be analyzed as one of the surgical videos of the database. By this technical means, the problems of the prior art can be solved, thereby achieving the technical effect of improving the efficiency of marking surgical videos.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A smart marking system for a surgical video, comprising:
a database for storing a plurality of organ eigenvalues, a plurality of surgical instrument eigenvalues, and a plurality of the surgical videos, each of the plurality of the surgical videos corresponding to a surgical name;
a feature generation module, connected to the database, for loading each of the plurality of the surgical videos of the database for image recognition separately, and loading the plurality of organ eigenvalues, the plurality of surgical instrument eigenvalues at the beginning, and generating at least one object information corresponding to each of the plurality of the surgical videos according to each image recognition result, and using the at least one object information as feature data of the surgical video corresponding thereto, and storing the feature data in the database, wherein each of the at least one object information comprises coordinates, proportions and time points of at least one matched images of the plurality of the organ eigenvalues or the plurality of the surgical instrument eigenvalues existing in the surgical video corresponding thereto;
an analysis module, connected to the database, for performing eigenvalue analysis and statistics according to a video to be analyzed and all the feature data after loading the video to be analyzed to calculate a similarity rate between the video to be analyzed and each of the plurality of the surgical videos;

a storage module, connected to the analysis module, for selecting the surgical name corresponding to the surgical video with the highest similarity rate to mark a surgical name corresponding to the video to be analyzed, and storing the video to be analyzed and the surgical name corresponding thereto in the database to make the video to be analyzed as one of the surgical videos of the database; and a segmentation module, configured for detecting a plurality of time points of said at least one matched images of the plurality of the organ eigenvalues or the plurality of the surgical instrument eigenvalues in each of the plurality of the surgical videos, and deleting a plurality of frames corresponding to a time interval in each of the plurality of the surgical videos to form a plurality of divided videos and storing the plurality of divided videos in the database when the time interval between the adjacent time points in which at least one of the organ eigenvalues and the surgical instrument eigenvalues is present is greater than a predetermined interval.

2. The smart marking system according to claim 1, wherein the feature generation module loads all the plurality of the surgical videos corresponding to the same surgical name to identify a type of a surgical instrument and a type, a shape and a size of an abnormal organ in each of the plurality of the surgical videos, and generate a starting eigenvalue corresponding to the surgical name according to each identification result, and stores each of the starting eigenvalues and the surgical name corresponding thereto in the database.

3. The smart marking system according to claim 2, wherein the analysis module compares the video to be analyzed with all the starting eigenvalues in the database, and loads the surgical name corresponding to the starting eigenvalue that matches the video to be analyzed as the surgical name corresponding to the video to be analyzed, wherein when the loaded surgical name is different from the surgical name selected according to the similarity rates, a prompt message is generated, and the loaded surgical name or the selected surgical name is chosen to be the surgical name corresponding to the video to be analyzed.

4. A smart marking method for a surgical video, comprising the steps:

providing a plurality of organ eigenvalues, a plurality of surgical instrument eigenvalues, and a plurality of surgical videos in a database, each of the plurality of the surgical videos corresponding to a surgical name;

loading each of the plurality of the surgical videos of the database separately for image recognition, and loading the plurality of organ eigenvalues, the plurality of surgical instrument eigenvalues at the beginning, and generating at least one object information corresponding to each of the plurality of the surgical videos according to each image recognition result, and using the at least one object information as feature data of the surgical video corresponding thereto, and storing the feature data in the database, wherein each of the at least one object information comprises coordinates, proportions and time points of at least one matched images of the plurality of the organ eigenvalues or the plurality of the surgical instrument eigenvalues existing in the surgical video corresponding thereto;

performing eigenvalue analysis and statistics according to a video to be analyzed and all the feature data after loading the video to be analyzed to calculate a similarity rate between the video to be analyzed and each of the plurality of the surgical videos;

selecting the surgical name corresponding to the surgical video with the highest similarity rate to mark a surgical name corresponding to the video to be analyzed, and storing the video to be analyzed and the surgical name corresponding thereto in the database to make the video to be analyzed as one of the surgical videos of the database; and detecting a plurality of time points of said at least one matched images of the plurality of the organ eigenvalues or the plurality of the surgical instrument eigenvalues in each of the plurality of the surgical videos, and deleting a plurality of frames corresponding to a time interval in each of the plurality of the surgical videos to form a plurality of divided videos and storing the plurality of divided videos in the database when the time interval between the adjacent time points in which at least one of the organ eigenvalues and the surgical instrument eigenvalues is present is greater than a predetermined interval.

5. The smart marking method according to claim 4, wherein the method further comprises the step: loading all the plurality of the surgical videos corresponding to the same surgical name to identify a type of a surgical instrument and a type, a shape and a size of an abnormal organ in each of the plurality of the surgical videos, and generate a starting eigenvalue corresponding to the surgical name according to each identification result, and storing each of the starting eigenvalues and the surgical name corresponding thereto in the database.

6. The smart marking method according to claim 5, wherein the method further comprises the step: comparing the video to be analyzed with all the starting eigenvalues in the database, and loading the surgical name corresponding to the starting eigenvalue that matches the video to be analyzed as the surgical name corresponding to the video to be analyzed, and when the loaded surgical name being different from the surgical name selected according to the similarity rates, generating a prompt message, and the loaded surgical name or the selected surgical name being chosen to be the surgical name corresponding to the video to be analyzed.

* * * * *